US012648546B2

(12) United States Patent
Klaas

(10) Patent No.: US 12,648,546 B2
(45) Date of Patent: Jun. 9, 2026

(54) METHOD AND CONTROL DEVICE FOR SURVEYING EATING BEHAVIOUR OF ANIMALS

(71) Applicant: DELAVAL HOLDING AB, Tumba (SE)

(72) Inventor: Ilka Klaas, Tumba (SE)

(73) Assignee: DeLaval Holding AB, Tumba (SE)

( * ) Notice: Subject to any disclaimer, the term of this patent is extended or adjusted under 35 U.S.C. 154(b) by 56 days.

(21) Appl. No.: 18/573,271

(22) PCT Filed: Jun. 21, 2022

(86) PCT No.: PCT/SE2022/050612
§ 371 (c)(1),
(2) Date: Dec. 21, 2023

(87) PCT Pub. No.: WO2022/271067
PCT Pub. Date: Dec. 29, 2022

(65) Prior Publication Data
US 2024/0284876 A1      Aug. 29, 2024

(30) Foreign Application Priority Data

Jun. 23, 2021    (SE) .................................... 2150812-2

(51) Int. Cl.
A01K 1/10        (2006.01)
A01K 1/00        (2006.01)
(Continued)

(52) U.S. Cl.
CPC .......... A01K 29/005 (2013.01); A01K 1/0023 (2013.01); A01K 5/0275 (2013.01);
(Continued)

(58) Field of Classification Search
CPC .. A01K 29/005; A01K 1/0023; A01K 11/006; A01K 1/105; A01K 5/02;
(Continued)

(56) References Cited

U.S. PATENT DOCUMENTS 4,463,353  A  *  7/1984  Kuzara .................... G07C 9/28
                                                    340/10.5
6,427,627  B1     8/2002  Huisma
                          (Continued)

FOREIGN PATENT DOCUMENTS

EP            0624313  A1    11/1994
EP            2109358  A1    10/2009
                          (Continued)

OTHER PUBLICATIONS

International Search Report for PCT/SE2022/050612 mailed Sep. 12, 2022, 5 pages.
(Continued)

*Primary Examiner* — Magdalena Topolski
*Assistant Examiner* — Spencer T Callaway
(74) *Attorney, Agent, or Firm* — NIXON & VANDERHYE

(57)          ABSTRACT

Disclosed is a method for managing animals by surveying eating behavior of the animals in a livestock area, including monitoring the animals over a time period subsequent to distributing feed at a feed table in the livestock area, identifying animal behavior that fails to meet a criteria, and performing an such as regrouping the animals or conducting a health check on the animals.

19 Claims, 3 Drawing Sheets

(51) Int. Cl.

| | | |
|---|---|---|
| *A01K 5/02* | (2006.01) |
| *A01K 11/00* | (2006.01) |
| *A01K 29/00* | (2006.01) |
| *A61B 5/11* | (2006.01) |

(52) U.S. Cl.
CPC ........... *A01K 11/006* (2013.01); *A61B 5/1118* (2013.01); *A61B 2503/40* (2013.01)

(58) Field of Classification Search
CPC .. A01K 5/0275; A01K 5/0291; A61B 5/1118; A61B 2503/40
See application file for complete search history.

(56) References Cited

U.S. PATENT DOCUMENTS

| | | | | |
|---|---|---|---|---|
| 6,868,804 B1* | 3/2005 | Huisma | .................. | A01K 29/00 |
| | | | | 119/842 |
| 7,705,736 B1* | 4/2010 | Kedziora | ............. | A01K 27/009 |
| | | | | 340/573.3 |
| 10,045,511 B1 | 8/2018 | Yarden et al. | | |
| 2008/0128486 A1* | 6/2008 | Lowe | .................... | A01K 67/02 |
| | | | | 235/492 |
| 2011/0192213 A1* | 8/2011 | Zimmerman | ............ | A01K 5/02 |
| | | | | 73/23.3 |
| 2017/0118961 A1 | 5/2017 | Halachmi et al. | | |
| 2017/0325422 A1* | 11/2017 | Van Den Berg | ..... | A01K 5/0208 |
| 2019/0053470 A1* | 2/2019 | Singh | ................... | A01K 11/004 |
| 2019/0380311 A1 | 12/2019 | Crouthamel et al. | | |
| 2023/0189763 A1* | 6/2023 | Blanc | ..................... | G01S 7/023 |
| | | | | 340/573.3 |

FOREIGN PATENT DOCUMENTS

| | | | |
|---|---|---|---|
| EP | 3316680 A1 | 5/2018 |
| EP | 3494779 A1 | 6/2019 |
| WO | 2008089472 A1 | 7/2008 |
| WO | 2010066429 A1 | 6/2010 |
| WO | 2015145422 A1 | 10/2015 |
| WO | 2018111180 A1 | 6/2018 |

OTHER PUBLICATIONS

Written Opinion of the ISA for PCT/SE2022/050612 mailed Sep. 12, 2022, 10 pages.
Swedish Search Report for SE2150812-2 mailed Feb. 4, 2022, 3 pages.

* cited by examiner

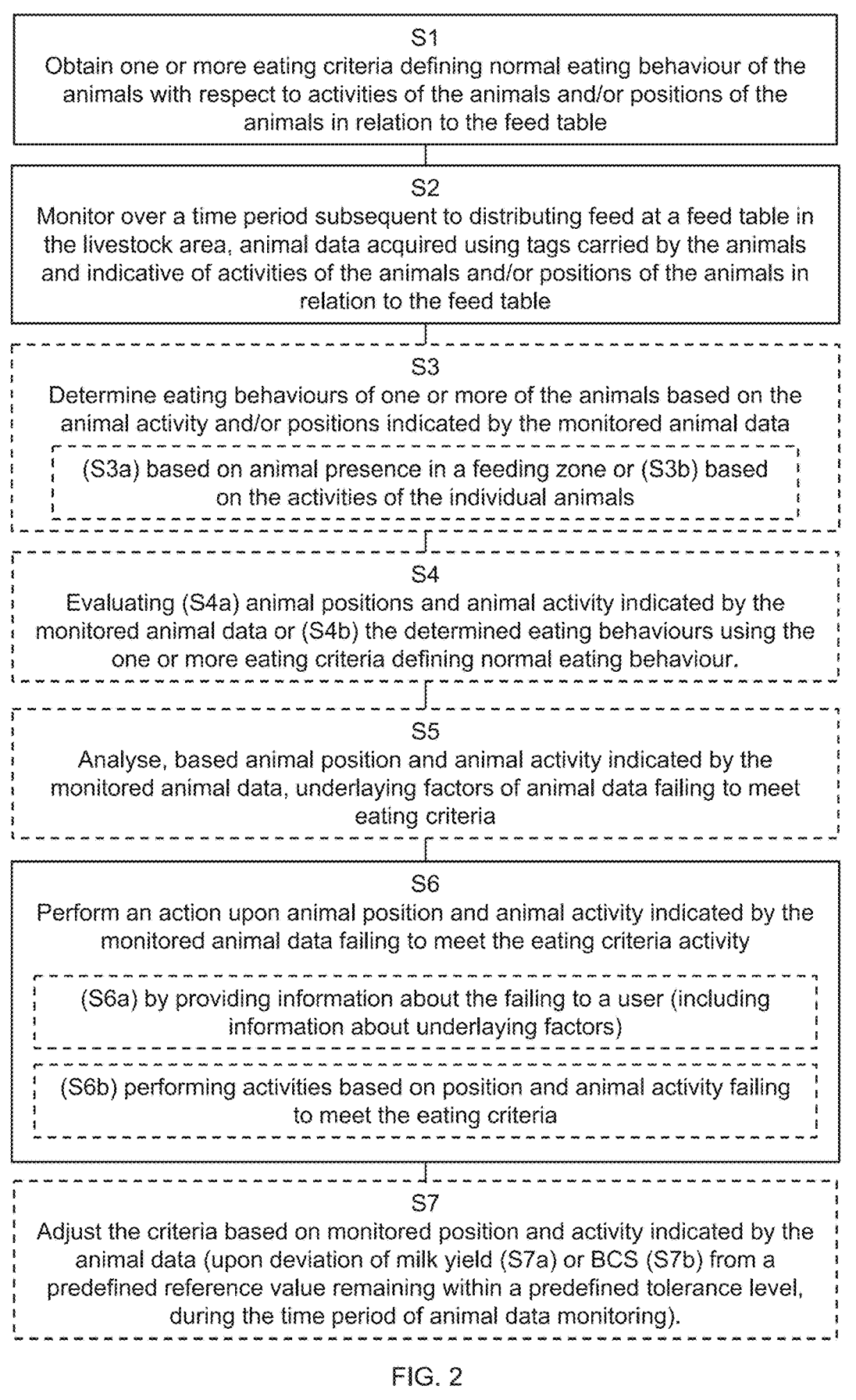

S1
Obtain one or more eating criteria defining normal eating behaviour of the animals with respect to activities of the animals and/or positions of the animals in relation to the feed table

S2
Monitor over a time period subsequent to distributing feed at a feed table in the livestock area, animal data acquired using tags carried by the animals and indicative of activities of the animals and/or positions of the animals in relation to the feed table

S3
Determine eating behaviours of one or more of the animals based on the animal activity and/or positions indicated by the monitored animal data (S3a) based on animal presence in a feeding zone or (S3b) based on the activities of the individual animals

S4
Evaluating (S4a) animal positions and animal activity indicated by the monitored animal data or (S4b) the determined eating behaviours using the one or more eating criteria defining normal eating behaviour.

S5
Analyse, based animal position and animal activity indicated by the monitored animal data, underlaying factors of animal data failing to meet eating criteria

S6
Perform an action upon animal position and animal activity indicated by the monitored animal data failing to meet the eating criteria activity (S6a) by providing information about the failing to a user (including information about underlaying factors)

(S6b) performing activities based on position and animal activity failing to meet the eating criteria

S7
Adjust the criteria based on monitored position and activity indicated by the animal data (upon deviation of milk yield (S7a) or BCS (S7b) from a predefined reference value remaining within a predefined tolerance level, during the time period of animal data monitoring).

FIG. 2

METHOD AND CONTROL DEVICE FOR SURVEYING EATING BEHAVIOUR OF ANIMALS

CROSS-REFERENCE TO RELATED APPLICATIONS

This application is the U.S. national phase of International Application No. PCT/SE2022/050612 filed Jun. 21, 2022 which designated the U.S. and claims priority to SE 2150812-2 filed Jun. 23, 2021, the entire contents of each of which are hereby incorporated by reference.

TECHNICAL FIELD

The present disclosure generally relates to feeding animals and in particular to a method for surveying eating behaviour of animals in a livestock area. The disclosure also relates a control device, and to a computer program for performing the method.

BACKGROUND

Feeding dairy animals, or other livestock, is an important daily routine for farmers. The animals receive, for example, roughage or totally or partially mixed rations at a feed table or feed fence. Regular feed intake is necessary for animals to ensure high feed intake to maintain a healthy body that can support high milk production and pregnancy. Hence, ensuring that each animals can eat what they need is of high importance to maintain a high milk production.

However, various factors like overcrowding, aggressions at the feed table, compromised health status and other factors can influence the number of visits of an animal to the feeding zone, the feed table and as a consequence the feed intake.

A method to provide animals, such as e.g. cows, with a correct amount of feed is presented in WO2018111180A1, which proposes grouping animals based on information on body condition score (BCS) in order to able to provide an optimal amount of energy to each animal.

However, sometimes it is desirable to take measure to assure that animals can eat what they need already before BCS is affected. Hence, there is a need for improved methods that can assist farmers in assuring that animals can eat what they need.

SUMMARY

It is an object of the disclosure to alleviate at least some of the drawbacks with the prior art. Thus, it is an object to provide a method for surveying eating behaviour of animals in a livestock area. In particular it is an object to achieve a method for surveying animals eating behaviour that makes it possible to perform measures before deviating eating behaviour affects body condition and milk production of the animals.

According to a first aspect, the disclosure relates to a method for surveying eating behaviour of animals in a livestock area. The method comprises monitoring over a time period subsequent to distributing feed at a feed table in the livestock area, animal data acquired using tags carried by the animals and indicative of activities of the animals and/or positions of the animals in relation to the feed table. The method further comprises performing an action upon the monitored animal data failing to meet one or more eating criteria defining normal eating behaviour of the animals with respect to activities of the animals and/or positions of the animals in relation to the feed table. The proposed method makes it possible to detect deviant eating behaviour before consequences like a deviating BCS and decreasing milk production occur. Thereby, it is possible to perform measures to mitigate deviant eating behaviours and avoid that body condition and milk production of the animals is affected when needed. The method facilitates utilizing available resources in the most efficient way while ensuring well-being of the animals and enabling immediate intervention when eating behaviour changes.

According to some embodiments, the one or more eating criteria can be used to evaluate eating behaviour from one or more of animal position, animal movement, animal pose, chewing activity, animal velocity indicated by the animal data. By evaluating a variety of animal parameters a better estimation of eating behaviour can be made.

According to some embodiments, the one or more eating criteria comprises individual eating criteria of individual animals, eating criteria valid for a subset of the animals and/or common eating criteria valid for all the animals. In some situations it is possible to use the same eating criteria for all animals in a herd, which facilitates surveillance. By tailoring the eating criteria for individuals or groups of animals more accurate evaluation is enabled in other scenarios.

According to some embodiments, the method comprises determining eating behaviours of one or more of the animals based on the activities and/or positions indicated by the monitored animal data and evaluating the determined eating behaviours using the one or more eating criteria defining normal eating behaviour. By first determining eating behaviour from the animal data, it is possible to compare the actual behaviour to normal eating behaviour defined by the criteria.

According to some embodiments, the determined eating behaviours comprises one or more of; time present at feed table, time pattern of time present at feed table, actual eating time, time pattern of actual eating time, eating or chewing rate, stress level while eating, movement while eating, pose while eating and position at feed table. Hence, a variety of behaviours associated with eating may be evaluated to determine whether eating behaviour is normal.

According to some embodiments, the method comprises analysing position and animal activity indicated by the monitored animal data to determine underlying factors of the animal data failing to meet eating criteria, upon the monitored animal data failing to meet the one or more eating criteria. Hence, a reason for an abnormal eating behaviour may also be determined, which facilitates mitigating abnormal eating behaviour.

According to some embodiments, the analysing underlying factors comprises detecting positions and/or activity indicative of one or more of overcrowding, aggressive behaviour of animals and displacement of animals. Thereby, underlying problems may be resolved by re-grouping or similar.

According to some embodiments, the performing an action comprises providing information to a user about the failing to meet the one or more eating criteria. Thereby, a farmer is informed about abnormal eating behaviour and can perform actions to avoid consequences in time.

According to some embodiments, the provided information is indicative of the determined one or more underlying factors of the failing to meet the one or more eating criteria. Thereby, a farmer will also be informed about what is the root cause of the abnormal eating behaviour.

According to some embodiments, the provided information comprises an instruction to perform an activity. Thereby, a farmer is informed about activities that can resolve the situation. In some embodiments, the automatically performing activity comprises adjusting a working schedule, trajectory, speed and or operation mode of the feed robot.

According to some embodiments performing an action comprises automatically performing an activity associated with the animals in the livestock area. Hence, sometimes an unwanted situation may be resolved without human interaction, by for example a farmer.

According to some embodiments, the action comprises one or more of; regrouping animals to other group, splitting up an animal pair or group of animals that influence each other's eating behaviour, instructing a health check and performing automated livestock management. By performing these actions decreased BCS and milk production may be avoided.

According to some embodiments, the method comprises adjusting the one or more eating criteria based on the position and activity indicated by the monitored animal data. Thereby, the eating criteria may be optimised for individual herds, which decreases the risk of false alarms etc.

According to some embodiments, the adjusting is performed upon deviation of milk yield or body condition score from a predefined reference value remaining within a predefined tolerance level, during the time period of animal data monitoring. Hence, the eating criteria is adjusted when it is confirmed that a certain behaviour is normal and does not affect body condition or milk production for a certain herd or group of animals.

The method according to any one of the preceding claims, wherein the monitoring is performed using a real-time location system (RTLS). Thereby, the method may be implemented without additional hardware if an RTLS is already deployed.

According to a second aspect, the disclosure relates to a control device for monitoring eating behaviour of animals in a livestock area, wherein the control device is configured to perform the method according to the first aspect.

According to a third aspect, the disclosure relates to a computer program comprising instructions which, when the program is executed by a computer, cause the computer to carry out the method according to the first aspect.

According to a fourth aspect, the disclosure relates to a computer-readable medium comprising instructions which, when executed by a computer, cause the computer to carry out the method according to the first aspect.

BRIEF DESCRIPTION OF THE DRAWINGS

FIG. 2 is a flowchart of the proposed method for surveying eating behaviour of animals.

DETAILED DESCRIPTION

Regular access and long enough visits at a feed table are necessary for animals to ensure high feed intake to maintain a healthy animal body that can support high milk production and pregnancy. Animals that do not, or cannot, visit the feed table as often as they want, or eat as long as they want, may have impaired body condition, have lower milk yield and are at higher risk of getting diseases. Access to the feed table can be limited in cases of overcrowding or displacements of individual animals because of problems in the herd. In addition, if the palatability of the feed is lower, animals may be less motivated to eat. In other cases lower motivation to go to the feed table is caused by disorders or diseases.

A feed table is typically surrounded by an area where animals that are eating or that intend to eat are expected to reside. The proposed technique is based on the insight that by using animal data acquired using tags carried by the it is possible to monitor for example when animals enter a feeding zone and also their behaviour within the feeding zone. Depending on stage of lactation, milk production level and if the barns with an automated milking system (AMS) the milking permission, a maximum and minimum number of daily visits to the feeding zone and to the feed table may be defined. In addition, a time that an animal needs to stay at a position where it is able to reach the feed (for example with its head positioned above the feed table) to ensure a certain feed intake based on the animal's production level may also be defined. If one animal, or a group of animals, deviates from this predefined eating behaviour, an action should be taken. For example, an alarm is raised, so that a farmer can intervene and ensure access for this animal, or group of animals.

By analysing historical animal data it is also possible to identify an optimum number of animals that should reside in a certain part of the feeding zone to enable appropriate feed intake for all animals within the zone. This number can vary within herd and over time, dependent on feed quality and management (feeding times, animal traffic settings, feed pushing).

Figure 1:
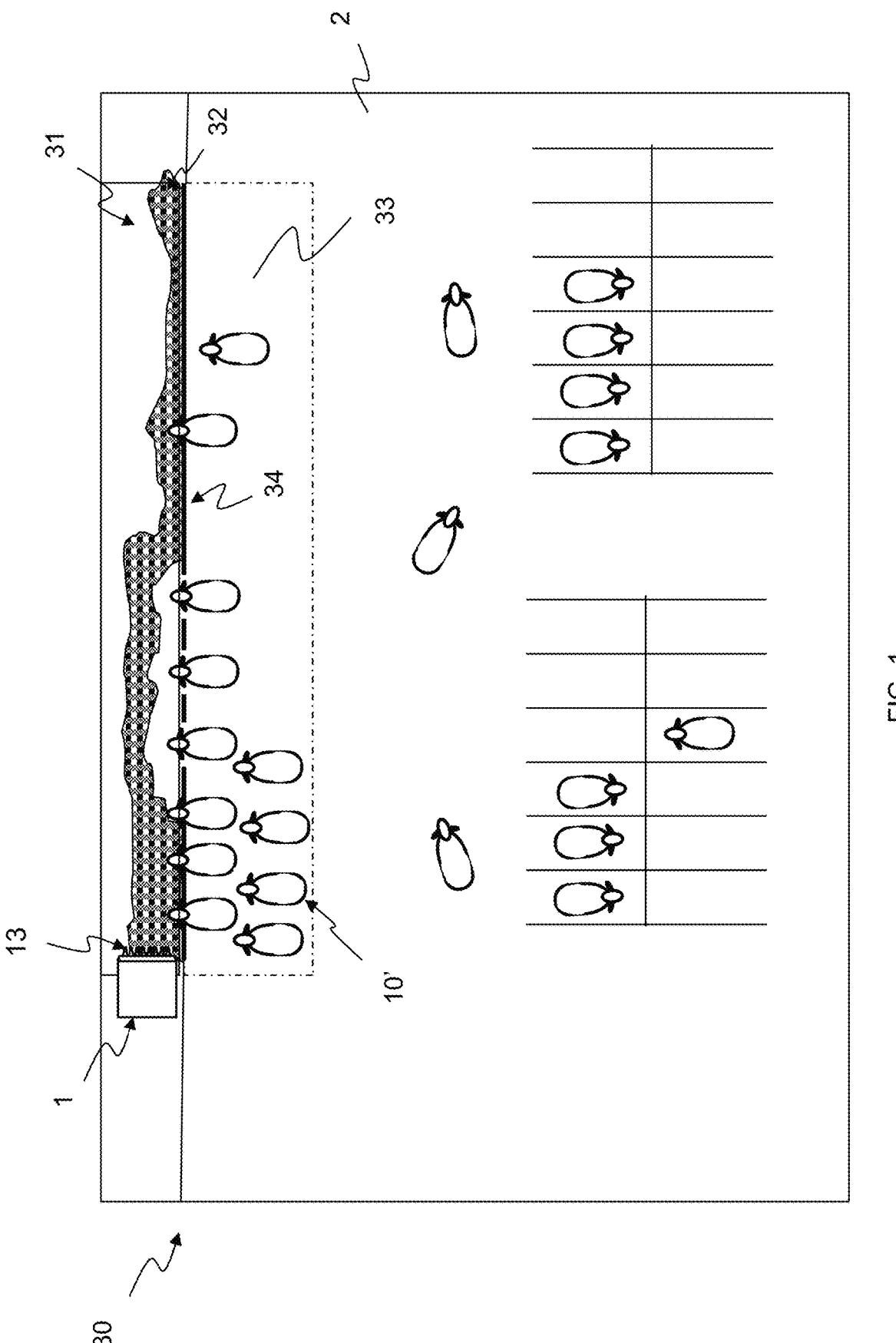
FIG. 1 is a top view of an example livestock area comprising a feed table.

The proposed technique will now be described in further detail with reference to FIGS. 1 to 4. FIG. 1 illustrates a feed table 31 arranged in a livestock area 30. The livestock area 30 comprises a dwelling area 2 in which the animals 10 are free to roam, cubicles 4, and a feed robot 1. The proposed technique is suitable to dairy animals such as e.g. cow, buffalo, sheep or goat.

A feed table 31 herein refers to any surface where feed is disposed and does not need to be a separate arrangement, or it may be a part of the floor. In other words, a feed table 31, is an area where feed is distributed to be eaten by the animals. The feed table 31 typically comprises separate feed table parts arranged along one or more alleys in a livestock area 30, such as a barn. The feed table may comprise several (separate or connected) feed table parts, which may be seen as individual feed tables 31. However, for simplicity only one feed table 31 is illustrated. In this disclosure these individual feed tables 31 are referred to as one single feed table, as the feed table 31 is typically just a part of the floor, on which it is intended to put feed 32. The feed table 31 is typically divided into feeding places. In some embodiments, one feeding place is a head lock.

A feed fence 34 is arranged along the alleys between the feed table 31 and the animals 10. The feed fence 34 is arranged to separate the feed table 31 from the dwelling area 2. More specifically, the feed fence 34 is a barrier preventing the animals 10 from entering the feed table 31, but through which the animals can reach feed 32 positioned near the feed fence 34 by reaching their heads through the feed fence 34. Head locks arranged in the feed fence 34 are commonly used to fix the position of one animal 10 to one feeding place.

When an animal wants to eat it moves towards the feed table 31. It may be assumed that most animals that reside in a feeding zone 33 close to the feed table 31, for example in the alley right next to the feed table 31, are there because they are eating, have eaten or intend to eat. Stated differently, the feeding zone 33 is defined as a predefined area of the livestock area 30, close to the feed fence 34. In other words, a predefined area in which an animal that is eating or is attempting to eat is expected to reside, is herein referred to as a feeding zone 33. The feeding zone 33 may be defined differently depending the livestock area 30 and the feed table 31. Hence, the feeding zone 33 is typically predefined based on the design of the barn and observations about eating behaviour. For example, the feeding zone 33 is an area within a predetermined distance e.g. 3, 4 or 5 meters) from the feed fence 34 on the side of the feed fence 34 where the animals 10 are able access the feed 32.

The feed robot 1 is operating along the feed table 31. The feed robot 1 comprises a feed distribution mechanism 13 configured to deliver and/or redistribute feed in a livestock area 30. In the illustrated example the feed distribution mechanism 13 is a feed redistribution mechanism configured to redistribute or move feed 32. The illustrated feed redistribution mechanism comprises a rotating auger. The rotating auger lifts, mixes, and aerates the feed 32 while repositioning feed closer to a feed fence. However, other possible implementations of the feed redistribution mechanism comprise a barrel, a skirt, a plough or some other kind of feed redistribution mechanism. The feed robot may be automatically operated by a livestock management system 20.

Figure 4:
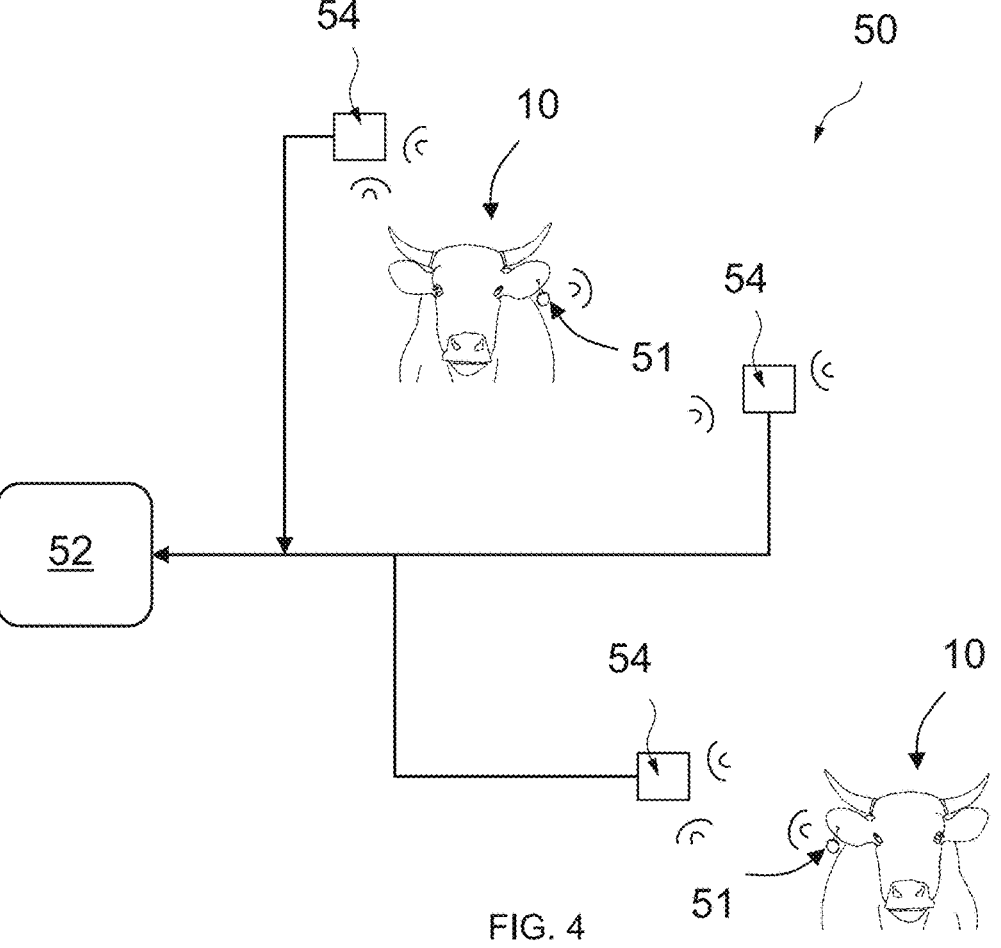
FIG. 4 illustrates a control device according to the second aspect.

The animals 10 in the livestock area 30 are carrying tags 51 (see FIG. 4). Animal data indicative of positions of the animals 10 in the livestock area 30 in relation to a feed table is acquired using the tags. According to some embodiments the tags are configured to acquire activity data. For example, the tags may comprise a motion sensor or an accelerometer configured to measure rate or change of velocity. If the tags are positioned on the animal's heads, or necks, they may be used to determine head movement and eating activity such as chewing and/or swallowing. Different techniques to determine eating behaviours of individual animals from accelerometer data are known in the field of farming. One example is described in "Development of an automatic classification system for eating, ruminating and resting behavior of cattle using an accelerometer", Grassland Science (ISSN1744-6961), Volume 54 Issue 4 pages 231-237, December 2008.

In some embodiments, the animal data is indicative of activity of the animals 10, such as activities associated with eating. For example, the animal data is indicative of chewing activity associated with eating, animal pose etc. Note that chewing activity associated with eating shall be differentiated form chewing associated with ruminating, for example by analysing chewing pattern or in addition studying the pose of the animal or whether the animal is opening its mouth. The animal data may also be indicative of behaviour that may potentially disturb eating of the animal or of other animals, such as abnormal animal movement that could be a sign of aggression or stress.

The animal data is for example provided by a Real Time Location System, RTLS, installed in the livestock area 30. An RTLS 50 is a known type of system used to track the location of objects, such as animals 10, in real time using tags 51 attached to animals 10 located in a livestock area 30 as the one in FIG. 1. Hence, if an RTLS 50 is already available the proposed technique can use animal data provided by the already installed RTLS 50. An RTLS 50 will be described in further detail below in connection with FIGS. 3 and 4.

In alternative embodiments, the tags 51 are in direct communication with one or more of a plurality of tag readers (not illustrated) arranged in the livestock area 30. In these embodiments, the tags 51 may be configured to record animal data including activity data. In some embodiments the positions of the animals 10 are determined based on relative distance to one or more of the tag readers. For example, the position is determined based on ability to communicate wirelessly with one or more of the access point using near field communication. The animal data is then communicated from the tags 51 to one or more of the tag readers.

Figure 3:
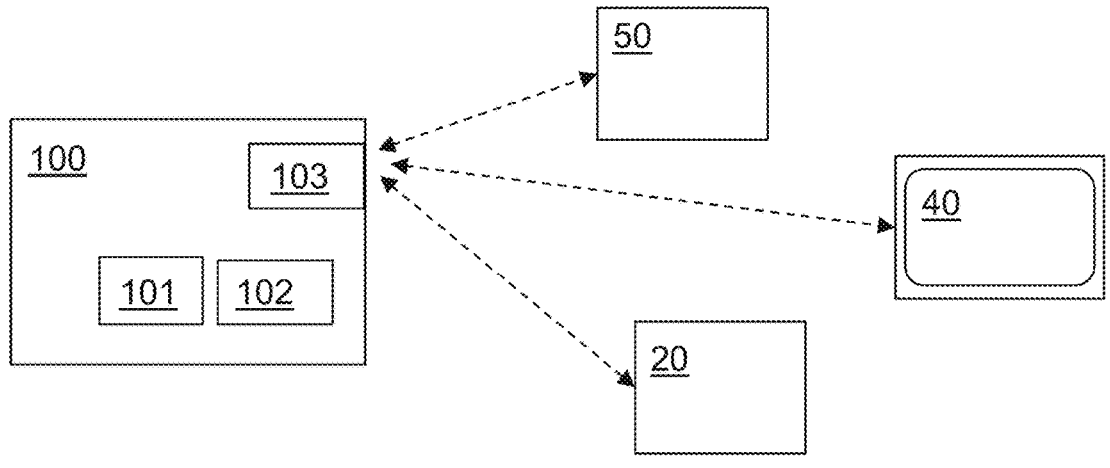
FIG. 3 is a conceptual illustration of a real time location system.

The proposed technique will now be described in further detail with reference to the flow chart of FIG. 2 and the livestock area 30 of FIG. 1. FIG. 2 is a flow chart of an exemplifying method for surveying eating behaviour of animals 10 in a livestock area 30. The method illustrated in FIG. 2 is e.g. performed by control device 100. The control device 100 for example a control device 100 of a livestock management system 20 (FIG. 3).

The method may be implemented as a computer program comprising instructions which, when the program is executed by a computer e.g. a processor in the control device), cause the computer to carry out the method. According to some embodiments the computer program is stored in a computer-readable medium e.g. a memory or a compact disc) that comprises instructions which, when executed by a computer, cause the computer to carry out the method.

The proposed method is based on the idea of evaluating animal position and activity using eating criteria defining normal eating behaviour. This evaluation reveals if eating behaviour is normal or if there is a risk of malnutrition. The criteria comprise for example a set of conditions or an algorithm that is used to determine if positions and activities of the animals 10 in a livestock area 30 correspond to normal eating behaviour. Normal eating behaviour is defined as behaviour that would typically maintain a good body condition and milk production for animals of the same type in general. Body condition may be evaluated for example by body condition scoring (BCS), which is tool designed to assess body reserves or fat accumulation of an animal. A default normal eating behaviour is typically determined by studying a large number of animals in a similar environment. However, as animals are individuals, what is "normal" may differ and also change over time. Hence, the eating criteria may be adjusted or adapted to fit a certain livestock area 30.

The method is typically performed continually when animals are dwelling in the livestock area 30. The method is based on surveying animal's eating behaviour by evaluating animal data using eating criteria. In some embodiments the method comprises obtaining S1 one or more eating criteria defining normal eating behaviour of the animals with respect to activities of the animals and/or positions of the animals in relation to the feed table. Obtaining S1 herein refers to receiving or retrieving the eating criteria. For example, eating criteria is received from an external server. Alternatively eating criteria is retrieved via configuration via a user interface of a user device 40 (FIG. 4) and/or by reading default criteria from a memory.

Initial eating criteria may be preconfigured at manufacturing or programmed during installation of the control device 100 configured to perform the method. The eating criteria define one or more conditions that need to be fulfilled for eating behaviour to be considered "normal". Normal eating behaviour corresponds to eating behaviour that maintains good body condition and well-being of the animals and is defined by professionals studying behaviour of healthy animals. What is normal does of course vary between different herds. Hence, initial or preconfigured eating criteria typically define what is normal for the average animal. If eating criteria is configured by a farmer via a user interface, then the eating criteria may be based on the farmer's knowledge about what is normal for a particular herd. The eating criteria may for example define ranges or minimum/maximum values that are normal for various parameters associated with eating, such as position, movement etc.

For example, the obtained eating criteria defining normal eating behaviour defines number of visits in a feeding zone, time spent in feeding zone, time between entering feeding zone 33 and accessing feed table, displacement within feeding zone 33, stationary time in feeding zone 33 or occupancy in feeding zone 33 or parts of feeding zone 33. The eating criteria will be described in more detail in connection with examples below. The eating criteria may be static or dynamic. In other words, in some embodiments it may be updated over time to better match what is "normal" for a particular herd.

Animals are then monitored to investigate if their eating behaviours are within normality. This is done using animal data acquired using tags that is obtained for example from an RTLS (FIG. 4). In other words, the method comprises monitoring S2 over a time period subsequent to distributing feed at a feed table in the livestock area 30, animal data acquired using tags carried by the animals 10. Monitoring S1 herein refers to obtaining animal data acquired at a plurality of different points in time. For example, animal data is provided in real time by an RTLS. Alternatively, the animal data is received now and then. For example, animal data is stored in the tags and retrieved from the tags when the animals get close to a tag reader. Tag readers are typically available around the feed table 31 and/or in the feeding zone 33.

That animal data is monitored subsequent to distributing feed typically refer to directly or soon after distributing feed, when feed is still available at the feed table. In some embodiments, animal data is monitored repetitively with regular intervals such as every 1-2 second) all the time as new feed is typically distributed when most of, or part of, the feed has been consumed.

The animal data is indicative of activities of the animals and/or positions of the animals in relation to the feed table 31. For example, the animal data is indicative of real-time positions given by for example coordinates in a reference coordinate system of the livestock area 30. A RTLS 50 may position animals 10 with an accuracy below (i.e. more accurate than) one meter. The positions may also be less accurate. In some embodiments the positions are represented by identity of the closest tag reader of an animal 10. The activities indicated by the animal data comprises for example animal movement, animal pose, chewing activity, animal velocity etc.

From the monitored animal data indicative of activities of the animals and/or positions of the animals in relation to the feed table 31 it is possible to assess animal behaviour. For example, a position and activity of an animal may be analysed over time to determine how many times (and/or how long time) the animal has been eating. In addition the animal's pose may indicate if it is able to eat (i.e. likely or possibly eating), for example if its head is above the feed for example in a headlock. If an animal is stationary in the feeding zone 33 (or within a certain distance from the feed table 31 where it may reach feed 32) and is also performing activity associated with eating, then it may be assumed that the animal is eating during that time. Another example is that an animal that is moving around extensively in the feeding zone 33 may be determined to be stressed while eating. In other words, in some embodiments, the method comprises determining S3 eating behaviours of one or more of the animals based on the activities and/or positions indicated by the monitored animal data. A variety of different eating behaviours may be determined based on the animal data, such as time present at feed table, time pattern of time present at feed table, actual eating time, time pattern of actual eating time, eating or chewing rate, stress level while eating, movement while eating, pose while eating and position at feed table.

The animal data may then be directly analysed using one or more predetermined criteria to determine if the animal data correspond to normal eating behaviour. For example, the position of each animals is tracked to reveal a number of visits to the feeding zone 33. The number of visits express the intention of the animal to go eating. If a count of animal visits is too low, it is an indication of bad health, herd related problems or some other reason. Animals with low rank may fear entering the feeding zone 33. In other words, in some embodiments, the method comprises evaluating S4*a* animal positions and animal activity indicated by the monitored animal data using the one or more eating criteria defining normal eating behaviour.

Alternatively, if eating behaviour have been the determined S3, then the determined eating behaviours are analysed using the predetermined criteria. Stated differently, in these embodiments the criteria do not define what is normal in terms of position or activity of the animal but rather with regards to certain eating behaviour that is determined S3 based on the position and activity. In other words, in some embodiments, the method comprises evaluating S4*b* the determined eating behaviours using the one or more eating criteria defining normal eating behaviour. For example, when an animal 10 has entered the feeding zone 33 the animal should within short time get to the feed table and remain there while eating for a duration of up to 30 min. In some embodiments, the one or more criteria defines an acceptable ratio between actual eating time and time spent in feeding zone 33. The determined eating behaviour is then compared to this ratio to evaluate if eating behaviour of an individual animal is normal. In other words, in some embodiments, the one or more eating criteria defines an acceptable time between entering feeding zone 33 and accessing feed table.

The eating criteria may specify normal eating behaviour per individual animal, on group level or for the entire herd. For example, a normal time that an individual needs to be present at feed table 31 will of course depend on how much feed it requires. Feed intake may also be defined for different groups defined by parameters like body weight, lactation, age etc. In other words, some embodiments, the one or more eating criteria comprises individual eating criteria of individual animals, eating criteria valid for a subset of the animals and/or common eating criteria valid for all the animals.

An example of behaviour that would not meet the eating criteria is that the animals 10 eat too little in comparison to a predefined (possibly animal specific or group specific) feed intake. The actual amount to be compared with the normal amount may be revealed from number of visits in feeding zone 33 and/or time spent in feeding zone 33. In other words, in some embodiments, the one or more eating criteria defining normal eating behaviour defines a number of visits in a feeding zone 33 and in some embodiments, the one or more eating criteria defining normal eating behaviour defines time spent in feeding zone 33.

If animals enter the feeding zone 33, but do not proceed to the feed table 31 or are displaced from the feed table by other animals, this will also be monitored and evaluated by the eating criteria as it may cause lowered feed intake. In other words, in some embodiments, the one or more eating criteria defining normal eating behaviour defines displacement within feeding zone 33.

The animal's behaviour while in the feeding zone 33 is typically also relevant here. Normally, an animal will enter the feeding zone 33, move to the feed table 31 and be stationary there while eating. Extensive movement may be an indicator that there is queue, that the animal is fighting with another animal or that it is stressed. This might in turn affect eating and result in low feed intake. In other words, in some embodiments, the one or more eating criteria defining normal eating behaviour defines stationary time in feeding zone 33.

If the evaluating S4*a*, S4*b* reveals that the animal data does not meet the eating criteria there is typically one or more underlying factors. The animal data may be further analysed to determine such factors. For example, if there are many animals 10 that eat too little, there is typically a general problem with the feed, with access to feed or a problem in the environment. However, if only one or a few individuals show deviating eating behaviour the cause is typically related to the individual. In other words, in some embodiments, the method comprises analysing S5 position and animal activity indicated by the monitored animal data to determine underlying factors of the animal data failing to meet eating criteria, upon the monitored animal data failing to meet the one or more eating criteria.

Underlying factors may for example be determined by analysing positions of the animals. For example, if there are too many animals in the feeding zone 33, overcrowding may cause stress and be the reason for changed eating behaviour. Overcrowding may easily be detected by counting animals per area unit and comparing the count with a reference value. Alternatively, based on the position of the animal 10 in relation to other animals it can be determined if there were more animals than feeding spaces, which may serve as an overcrowding indicator. In other words, in some embodiments, the analysing S5 underlying factors comprises detecting positions and/or activity indicative of overcrowding in the livestock area 30 or in parts of the livestock area 30.

Alternatively, the abnormal eating behaviour may be caused by one or more aggressive animals. By analysing the animal data it is possible to find correlation between presence of (or proximity to) certain individual animals. If abnormal eating behaviour often or always occur around a certain animal, then the underlying factor may be that the certain animal is aggressive. In other words, in some embodiments, the analysing S5 underlying factors comprises detecting positions and/or activity indicative of aggressive behaviour of one or more animals. Aggression and overcrowding may be analysed together as the aggressive behaviour at the feed table can be caused by overcrowding.

Another reason for abnormal eating behaviour may be displacement around the feed table 31. For example, many animals attempt to eat at the same place. In other words, in some embodiments, the analysing S5 underlying factors comprises detecting positions and/or activity indicative of displacement of animals. Displacement of an individual animal may also be caused by specific animals, as some animals tend to avoid the aggressive animals. Hence, aggression and displacement may be analysed together as the aggressive behaviour at the feed table can cause displacement.

Hence, aggressive behaviour at the feed table can be caused by overcrowding. Aggression may in turn cause displacement. Aggression may also be caused by a hierarchy of the animals, where some animals are aggressive to lower ranked animals. Based on aggressive interactions at the feed table the animals can be ranked and dominant aggressive animals as well as low ranking animals can be identified. In conclusion, by analysing a combination of overcrowding, aggressive behaviour and displacement, a root cause of the problem may be determined and mitigated.

If the animal's eating behaviour is deviating from the normal eating behaviour defined by the eating criteria, this should be remedied. In other words, the method comprises performing S6 an action upon the monitored animal data failing to meet one or more eating criteria defining normal eating behaviour of the animals 10 with respect to activities of the animals and/or positions of the animals in relation to the feed table 31. For example, if some animals do not enter the feeding zone 33 often enough per day, an alert is raised for the farmer to check health and well-being of these animals 10. If a livestock management system is implemented farmer interaction is not always required. A first attempt to fix the issue may be done by for example triggering a robot to perform an action.

Hence, abnormal eating behaviour is mitigated in different ways depending on the root cause. Measures may either be performed manually by a farmer or triggered to be performed automatically by an automated livestock management system or by a combination of these. In some embodiments performing S6 an action comprises providing S6*a* information to a user about the failing to meet the one or more eating criteria. The information may be a message on a display of a user device (FIG. 4). The information may alternatively or in addition be audible or presented in any suitable way.

The information typically comprises information about existence of an eating problem and possibly also information about what the problem is, such as low feed intake or stress. The information may also include an indication about underlying factors determined S5 based on the animal data. For example, a message may say: "Low feed intake in zone X" and "Possible cause overcrowding in zone X and lack of feed in zone Y". In other words, in some embodiments the provided information is indicative of the determined one or more underlying factors of the failing to meet the one or more eating criteria.

The information provided to a user may also include an intervention suggestion. For example, the information may suggest moving too dominant or too weak animals from the respective feeding zones. In addition, overcrowding alarm may be given for a specific part of a feeding zone 33 or the whole feeding zone 33. Are only parts of the feeding zone 33 overcrowded uneven distribution of feed or uneven animal traffic could be the underlying reason. In other words, in some embodiments, the provided information comprises an instruction to the user to perform an activity. Example activities that may be proposed are regrouping animals to other group, splitting up an animal pair or group of animals that influence each other's eating behaviour, instructing a health check and performing livestock management.

If an automated livestock management system is used some of the proposed activities may be performed automatically without any user's intervention. For example, feed distribution and/or pushing or regrouping is automatically performed by an autonomous feed robot or by an automated sort gate. In other words, in some embodiments performing S6 an action comprises automatically performing S6*b* an activity associated with the animals in the livestock area 30.

A feed robot 1 is typically operated according to an operation plan that comprises a schedule and a trajectory. The trajectory defines a route which defines where the feed robot 1 should drive and a corresponding velocity i.e. speed and travel direction. The schedule defines when the feed robot 1 should start operating along the trajectory. In some embodiments, the operation plan defines timings for sessions of the feed robot 1. More specifically a session herein refers to one operation session, which typically comprises one round, or run, in the livestock area 30. When the feed robot 1 is not operating, i.e. between the operating sessions, it is typically charged in a docking station.

An activity automatically performed S6*b* by a feed robot may be performed in different ways. In some embodiments, the automatically performing S6*b* an activity comprises triggering the feed robot 1 to start and/or stop operating. In other words, the schedule or times to operate the feed robot 1 is determined based on the deviating eating behaviour. This may be achieved by configuring an operation schedule or plan of the feed robot based on the deviating eating behaviour. For example, the animals may be tempted to eat more often if feed is distributed more often. In other words, in some embodiments the performing an action comprises generating a trigger causing a feed robot to start or stop operating.

In some embodiments automatically performing S6*b* an activity comprises controlling how or where the feed robot 1 operates. More specifically the method comprises adjusting a trajectory of a feed robot 1 operating in the livestock area. In this way it is possible to control where the feed robot 1 runs and how fast it runs, based on need indicated by the animals eating behaviour. In addition the activity of the feed robot may be controlled, such as what it does and where it does it. For example, the feed robot 1 may be controlled to have different operation modes, such as pushing feed and delivering feed (or simply just moving). Different operation modes may be activated in different places, based on need indicated by the eating behaviour. In other words, in some embodiments, the automatically performing S6*b* an activity comprises adjusting a trajectory, speed and or operation mode of the feed robot.

In some embodiments automatically performing S6*b* an activity comprises controlling a sort gate. For example, if a sort gate is arranged in a passage after milking, then the sort gate may be controlled to sort out aggressive animals or to split up animal pairs that fight.

The eating criteria may be static or dynamic. Dynamic criteria may be updated based on historic animal data. For example, if in a certain herd animal condition (represented by BCS) and milk production remains acceptable even under circumstances that deviate from some kind of normality average of many herds) then the eating criteria could be updated for this specific herd. Stated differently, it is typically a goal as such to maintain certain eating behaviour as long as the animals are feeling well. In other words, in some embodiments, the method comprises adjusting S7 the one or more eating criteria based on the position and activity indicated by the monitored animal data.

If a deviation in eating behaviour is detected and well-being is verified for example by health checks (maintained BCS), then this eating behaviour may be considered normal for this particular herd. In other words, in some embodiments, the adjusting S7 is performed upon deviation of milk yield S7*a* or body condition score S7*b* from a predefined reference value remaining within a predefined tolerance level, during the time period of animal data monitoring.

FIG. 3 illustrates a control device 100 for surveying eating behaviour of animals 10 in a livestock area 30, according to the second aspect in more detail. The control device 100 is communicates with a real time location system, RTLS, 50. In some embodiments the control device 100 is communicates with a user device 40 and/or with a livestock management system 20.

The user device 40 is a device that enables communication with a user, such as a farmer, such as a monitor, computer, tablet smartphone or similar. More specifically, the user device 40 is configured to provide information to a user, such as on a display. The user device 40 may also comprise speaker or other means to communicate with the user.

A livestock management system 20 is a system that assists farmers to record and keep track of their livestock. It may capture all events of an animal as well as keep track of most important dates in the lifetime of an animal. The livestock management system 20 may also be configured to perform livestock management automatically for example by automatically controlling a feed robot 1 (FIG. 1) and/or a sort gate (not shown).

In some embodiments the control device 100 is a functional unit. Hence, the control device 100 may be distributed between a plurality of physical control units, some of which may be located in the livestock area 30 and some of which may be remote from the livestock area 30. In some embodiments, the control device 100 is at least partly implemented in the feed robot 1. In some embodiments, the control device 100 is included in the livestock management system.

The control device 100 comprises hardware and software. The hardware is for example various electronic components on a for example a Printed Circuit Board, PCB. The most important of those components is typically a processor 101 e.g. a microprocessor, along with a memory 102 e.g. EPROM or a Flash memory chip. The software is typically software code that runs in the microcontroller. The illustrated control device 100 also comprises a communication interface 103. The communication interface 103 is configured for communication of signals and/or data between the control device 100 and other devices, such as the feed robot 1 and the RTLS, 50. The communication interface 103 is configured for wireless communication, using any suitable protocol e.g. Bluetooth or IEEE 802.11. The communication interface 103 may also be configured for wired communication, for example via a docking station. The communication interface 103 is for example configured to communicate with (a control system 52 (FIG. 4) of) the RTLS 50 and with the user device 40. In particular the control device 100 is configured to obtain animal data acquired using tags 51 (FIG. 4) carried by the animals 1. In some embodiments the communication interface 103 is configured to communicate with a remotely or locally arranged server.

More specifically the control device 100 is configured to monitor over a time period subsequent to distributing feed at a feed table in the livestock area 30, animal data acquired using tags carried by the animals 10 and indicative of activities of the animals and/or positions of the animals in relation to the feed table (31), and to perform an action upon the monitored animal data failing to meet the one or more eating criteria defining normal eating behaviour of the animals (10) with respect to activities of the animals and/or positions of the animals in relation to the feed table (31). In addition the control device 100 may be configured to perform one or more or all of the embodiments of the method described in connection with FIG. 2.

FIG. 4 illustrates an example of an RTLS 50 that may be used by the proposed method and control device 100. The RTLS also comprises readers 54 that receive wireless signals from these tags 51 to determine their locations. The wireless communication includes, but is not limited to, a cellular radio, a WiFi radio, a Bluetooth radio, a Bluetooth low energy radio, UltraWideBand radio or any other appropriate radio frequency communication protocol. The particular number and placement of the readers 54 will depend on the size and shape of a tracking zone 53, for example the livestock area 30, being monitored.

In some embodiments the tags 51 also comprise orientation sensors configured to generate data indicative of the orientation of the sensor, such as a three-axis accelerometer assembly or a gyro assembly. The tags 51 may also include other sensors or components, such as object monitoring sensors. The object monitoring sensors may comprise a thermometer, a heart rate monitor, a vibration sensor, a camera, a microphone, or any other appropriate device.

When the RTLS 50 is in use, the location of each tag 51 is tracked in real-time within the tracking zone 53 using multi-lateration techniques known in the art, for example using Time Difference of Arrival and Received Signal Strength Indicator techniques. To this end, data from the readers 54 is supplied to a control system 52 that determines, in real-time basis, the instantaneous position of each tag 51 in the tracking zone 53. The control system 52 may be implemented as a computer-based system that is capable of executing computer applications. An exemplary application of the control system 52 includes a real-time location function, configured to determine a two- or three-dimensional position of the tag 51 within a tracking zone 53. The control system 52 may for example use triangulation of data provided by three or more readers 54 to determine the location of the tags 51.

In some embodiments, the control system 52 is configured to determine a movement of the tags 51, including for example direction of movement and amount of movement. In some embodiments, the control system 52 is configured to determine an orientation of the tag 51. In some embodiments, the control system 52 is configured to discriminate between different activities of an animal 10 wearing the tag 51 based upon the location, movement and orientation of the animal's tag within the tracking zone 53. For example, the control system is configured to detect eating and/or activities associated with eating, such as chewing activity associated with eating.

The control system 52 may also have one or more communications interfaces. The communications interfaces may include for example, a modem and/or a network interface card. The communications interfaces enable the control system 52 to send and receive data to and from other computing devices such as a control device 10 of FIG. 3). The communications interface also enables the control system 52 to receive messages and data from the readers 54 or from the tags 51 either directly or via another communications network. The communications network may be any network platform and may include multiple network platforms. Exemplary network platforms include, but are not limited to, a WiFi network, a cellular network, etc.

The terminology used in the description of the embodiments as illustrated in the accompanying drawings is not intended to be limiting of the described method, control device or computer program. Various changes, substitutions and/or alterations may be made, without departing from disclosure embodiments as defined by the appended claims.

The term "or" as used herein, is to be interpreted as a mathematical OR, i.e., as an inclusive disjunction; not as a mathematical exclusive OR XOR), unless expressly stated otherwise. In addition, the singular forms "a", "an" and "the" are to be interpreted as "at least one", thus also possibly comprising a plurality of entities of the same kind, unless expressly stated otherwise. It will be further understood that the terms "includes", "comprises", "including" and/or "comprising", specifies the presence of stated features, actions, integers, steps, operations, elements, and/or components, but do not preclude the presence or addition of one or more other features, actions, integers, steps, operations, elements, components, and/or groups thereof. A single unit such as e.g. a processor may fulfil the functions of several items recited in the claims.

The invention claimed is:

1. A method for managing animals by monitoring eating behavior of the animals in a tracking zone of a livestock area comprising a feed table and a feeding zone close to the feeding table, the method comprising:

obtaining one or more eating criteria defining normal eating behavior of animals with respect to activities of the animals in relation to the feed table and with respect to positions of the animals in relation to the feed table, wherein at least one eating criterion defines a ratio between actual eating time and time spent in the feeding zone;

distributing feed at the feed table in the livestock area;

monitoring over a time period subsequent to distributing the feed, using a real-time location system (RTLS), animal data acquired using tags carried by the animals, the RTLS comprising readers that receive wireless signals from the tags to determine, on a real-time basis, the instantaneous position of each tag in the tracking zone, and the tags being attached to the animals' heads or necks and comprising a motion sensor or accelerometer, wherein the animal data is indicative of the activities of the animals in relation to the feed table and the positions of the animals in relation to the feed table;

determining eating behaviors of one or more of the animals based on the activities and positions indicated by the monitored animal data, the eating behaviors comprising an actual eating time;

evaluating the determined eating behaviors using the one or more eating criteria, including comparing a ratio between actual eating time and time spent in the feeding zone to evaluate whether the eating behavior of an individual animal is normal;

performing an action upon the determined eating behaviors failing to meet the one or more eating criteria, wherein the performing an action comprises providing information to a user that the one or more eating criteria were not met or comprises one or more of regrouping animals, splitting up an animal pair or group of animals, and conducting a health check on an animal.

2. The method according to claim 1 wherein the animal data comprises data that indicates activities of the animals in relation to the feed table and the indicated activities comprise one or more of animal movement, animal pose, chewing activity, and animal velocity.

3. The method according to claim 1 wherein the one or more eating criteria comprises individual eating criteria of individual animals, eating criteria valid for a subset of the animals, and/or common eating criteria valid for all the animals.

4. The method according to claim 1 wherein the feeding zone comprises a predefined area in which an animal that is eating or is attempting to eat is expected to reside and wherein the one or more eating criteria defining eating behavior defines one or more of:

number of visits in a feeding zone, time spent in feeding zone, time between entering feeding zone and accessing feed table, displacement within feeding zone, stationary time in feeding zone, and occupancy in feeding zone.

5. The method according to claim 1 further comprising:

evaluating animal positions and animal activity indicated by the monitored animal data using the one or more eating criteria defining eating behavior.

6. The method according to claim 1 wherein the determined eating behaviors comprise one or more of time present at feed table, eating or chewing rate, stress level while eating, movement while eating, pose while eating, and position at feed table.

7. The method according to claim 1 further comprising:

analyzing position and animal activity indicated by the monitored animal data to determine underlying factors of the animal data failing to meet eating criteria.

8. The method according to claim 7 wherein the analyzing underlying factors comprises detecting positions and/or activity indicative of one or more of overcrowding, aggressive behavior of animals, health status of animals, and displacement of animals.

9. The method according to claim 8 wherein the performing an action comprises the providing information to a user that the one or more eating criteria were not met.

10. The method of claim 9 wherein the provided information is indicative of the determined one or more underlying factors of the failing to meet the one or more eating criteria.

11. The method according to claim 10 wherein the provided information comprises an instruction to perform an activity.

12. The method according to claim 1 wherein performing an action comprises automatically performing an activity associated with the animals in the livestock area.

13. The method according to claim 1 further comprising adjusting the one or more eating criteria based on the position and activity indicated by the monitored animal data.

14. The method according to claim 13 wherein the adjusting is performed upon deviation of milk yield or a body condition score from a predefined reference value remaining within a predefined tolerance level, during the time period of animal data monitoring.

15. The method according to claim 1 wherein a feed robot is operated on the feed table according to an operation plan that comprises a schedule and a trajectory, and wherein performing an action comprises automatically performing an adjustment of a schedule, trajectory, speed and or operation mode of the feed robot.

16. A computer program comprising instructions which, when the program is executed by a computer, cause the computer to carry out the method according to claim 1.

17. A computer-readable medium comprising instructions which, when executed by a computer, cause the computer to carry out the method according to claim 1.

18. A control device for monitoring eating behavior of animals in a tracking zone of a livestock area comprising a feed table and a feeding zone close to the feed table, wherein the control device is configured to:

monitor, using a real-time location system, over a time period subsequent to distributing feed at a feed table in the livestock area, animal data acquired using tags carried by the animals, wherein the real-time location system comprises readers that receive wireless signals from the tags to determine, in real-time basis, the instantaneous position of each tag in the tracking zone, which tags are attached to the animal's heads, or necks, and comprising a motion sensor or accelerometer, and wherein the animal data is indicative of eating activities of the animals in relation to the feed table and positions of the animals in relation to the feed table;

determine eating behaviors of one or more of the animals based on the eating activities and positions indicated by the monitored animal data, wherein the eating behaviors comprises an actual eating;

evaluate the determined eating behaviors using the one or more eating criteria defining normal eating behavior, wherein the one or more eating criteria defines a ratio between actual eating time and time spent in the feeding zone and wherein the determined eating behavior is compared to this ratio to evaluate if the eating behavior of an individual animal is normal;

perform an action upon the determined eating behaviors failing to meet the one or more eating criteria defining normal eating behavior of the animals with respect to the eating activities of the animals in relation to the feed table and positions of the animals in relation to the feed table, wherein the performing an action comprises providing information to a user about the failing to meet the one or more eating criteria and/or wherein performing an action comprises automatically performing an activity associated with the animals in the livestock area, comprising one or more of; regrouping animals to other group, splitting up an animal pair or group of animals that influence each other's eating behavior, and instructing a health check.

19. The control device according to claim 18 wherein the control device is further configured to analyze position and animal activity indicated by the monitored animal data to determine underlying factors of the animal data failing to meet eating criteria, wherein the underlying factors comprise detecting positions and/or activity indicative of one or more of overcrowding, aggressive behavior of animals, and displacement of animals.

\*  \*  \*  \*  \*